United States Patent [19]

Agabian et al.

[11] Patent Number: 5,770,714
[45] Date of Patent: Jun. 23, 1998

US005770714A

[54] CHLAMYDIA MAJOR OUTER MEMBRANE PROTEIN

[75] Inventors: Nina Agabian, San Francisco; Richard Stephens, Oakland, both of Calif.; Cho-Chou Kuo, Seattle, Wash.; Guy Mullenbach, Oakland, Calif.

[73] Assignees: Washington Research Foundation, Seattle, Wash.; Chiron Corporation, Emeryville, Calif.

[21] Appl. No.: 466,814

[22] Filed: Jun. 6, 1995

Related U.S. Application Data

[62] Division of Ser. No. 144,095, Oct. 28, 1993, abandoned, which is a continuation of Ser. No. 691,639, Apr. 25, 1991, abandoned, which is a continuation of Ser. No. 818,523, Jan. 13, 1986, abandoned, which is a continuation-in-part of Ser. No. 692,001, Jan. 14, 1985, abandoned.

[51] Int. Cl.$^6$ .......................... C07H 21/02; C07H 21/04; C07K 5/00; C07K 13/00
[52] U.S. Cl. .................... 536/23.1; 536/24.3; 536/24.32; 536/24.33; 435/6; 435/91.2; 435/320.1; 435/240.2; 435/254.11; 435/254.2; 435/172.3; 435/69.1; 530/300; 530/350
[58] Field of Search ........................... 435/6, 91.2, 320.1, 435/240.2, 254.11, 254.2, 172.3, 69.1; 536/23.1, 24.3, 24.33, 265; 530/300, 350

[56] References Cited

U.S. PATENT DOCUMENTS 4,358,535  11/1982  Falkow et al. .............................. 435/5

OTHER PUBLICATIONS

Allan et al. Infection and Immunology 45:637–641, 1984.
Keller and Manak, In DNA Probes, Stockton Press, pp. 525–562, 1993.

*Primary Examiner*—W. Gary Jones
*Assistant Examiner*—Dianne Rees
*Attorney, Agent, or Firm*—Townsend and Townsend and Crew LLP

[57] ABSTRACT

Methods and compositions are provided for the production of a polypeptide which is immunologically cross-reactive with a naturally-occurring major outer membrane protein (MOMP) of *Chlamydia trachomatis*. A DNA construct including a replication system recognized by *E. coli*, and an MOMP gene under the transcriptional control of a β-galactosidase promoter and terminator is provided. Recombinant phage λgt11/L2/33 was deposited at the American Type Culture Collection, 12301 Parklawn Drive, Rockville, Md. 20852, on Jan. 10, 1985 and granted accession no. 40157. L2 B9-F DNA was deposited at the American Type Culture Collection on Dec. 31, 1985, and granted accession No. 40217.

13 Claims, 8 Drawing Sheets

FIG. 1A

```
     GluPheProLeuAspLeuLysAlaGlyThrAspGlyGluThrLysAspAlaSer
  1  GAATTCCCTCTTGATCTTAAAGCAGGAACAGATGGAGAGACAGGAACTAAGGATGCCTCT
     CTTAAGGGAGAACTAGAATTTCGTCCTTGTCTACCTCTCTGTCCTTGATTCCTACGGAGA
            <                                  <
     1 ecorl, 7 mnll, 13 mbol sau3a, 47 ddel, 51 fokl, 56 mnll, IleAspTyrHisGluTrpGlnAlaSerLeuAlaSerTyrArgLeuAsnMetPheThr
 61  ATTGATTACCATGAATGGCAAGCAAGTTTAGCTCTCTTACAGACTGAATATGTTCACT
     TAACTAATGGTACTTACCGTTCGTTCAAATCGAGAGAATGTCTGACTTATACAAGTGA
          <
     90 alul, 108 xmnl, ProTyrIleGlyValLysTrpSerArgAlaSerPheAspAlaAspThrIleArgTyrCys
121  CCCTACATTGGAGTTAAATGGTCTCGAGCAAGTTTTGATGCAGACACGATTCGGTATTGC
     GGGATGTAACCTCAATTTACCAGAGCTCGTTCAAAACTACGTCTGTGCTAAGCCATAACG
                                    <<                    <
     143 aval xhol, 144 tagl, 168 hinfl, 180 mnll, LeuSerProLysSerAlaThrThrValPheAspValThrThrLeuAsnProThrIleAla
181  CTCAGCCCGAAGTCAGTCAGCTACAACTGTCTTTGATGTTACCACTCTGAACCCAACTATTGCT
     GAGTCGGGCTTCAGTCAGTCGATGTTGACAGAAACTACAATGGTGAGACTTGGGTTGATAACGA
          <
     181 ddel, 195 alul,
```

FIG. 1B

```
     GlyAlaGlyAspValLysAlaSerAlaGluGlyGlyAspThrMetGlnIleVal
241  GGAGCTGGCGATGTGAAAGCTAGCGCAGAGGGTGGAGATACCATGCAAATCGTT
     CCTCGACCGCTACACTTTCGATCGCGTCTCCCAGTCTATGGTACGTTTAGCAA
                 ^
     243 alul, 258 alul, 263 hhal, 268 mnll, 275 alul, SerLeuGlnLeuAsnLysMetLysSerArgLysPheSerValLeuGlnAM
301  TCCTTGCAATTGAACAAGATGAAATCTAGAAAATTTCGGTATTGCAGTAGGAACAACTA
     AGGAACGTTAACTTGTTCTACTTTAGATCTTTTAAAGCCATAACGTCATCCTTGTTGAT
                                         ←
     325 xbal, 329 xmnl, 361  TTGTGGATGCAGACAAATACGCATTACAGTTGAGACTCGCTTGATCGATGAGAGAGCTGC
     AACACCTACGTCTGTTTATGCGTAATGTCAACTTGAGCGAACTAGCTACTCTCTCGACG
                                                              ^
     365 fokl, 394 hinfl, 403 mbol sau3a, 404 clal, 405 tagl, 415
     alul, 416 bbv fnu4hl, 421  TCACGTAAATGCACAATTCCGCTTCTAATTAATTGTATAATTTGTTAAACTTTGAAACCGTTC
     AGTGCATTTACGTGTTAAGGCGAAGATTAATTAACATATTAAAACAATTTGAAACCGTTC
                                                              ^
     523 ban2 hgiJll sdul, 527 tagl, 539 banl, 481  TTTATCTTTGTTAATAACGTTAATAACACTATCCGTGTTTCTGGGCTCGACTTCGGTCGG
     AAATAGAAACAATTATTGCAATTATTGTGATAGGCACAAGACCCGAGCTGAAGCCAGCC 523 ban2 hgiJll sdul, 527 tagl, 539 banl, 540 asul aya2,
```

FIG. 1C

```
541 GTCCAGTTTTTTGCAAAAATTTTTTTCTTACTTTCGATCTCCCTCCTATCTCTCTTA
    CAGGTCAAAAAAAACGTTTTTAAAAAAAGAATGAAAGCTAGAGGAGGATAGAGAGAAT
    577 tag1, 579 mbo1 sau3a, 585 mn11, 601 CAACAAAATCTAAAATTTCTCTAAAAGAAGATTGCATAAAAGGCCTCTTTCCAGTACTAT
    GTTGTTTTAGATTTTAAAGAGATTTTCTTCTAACGTATTTTCCGGAGAAAGGTCATGATA
    627 mbo11, 641 hae1 stu1, 642 hae111, 644 mn11, 653 sca1, 65
    4 rsa1, 661 ATCGGTCTACTTGAGCGCGGCGCCCGTAGCTCAATGGTAGAGAGCTGTAGCCTTCCAAGCTACCG
    TAGCCAGATGAACTCGCGCCGGGCATCGAGTTACCATCTCGACATCGGAAGGTTCGATGGC
    665 acc1, 675 hha1, 676 tac1, 677 hha1, 685 alu1, 698 alu1,
    713 alu1, 718 hpa11,
```

FIG. 2A

```
GGATCCTCACCCTCTTCATAAGCACGAATGCATTCTCTTAGGTTTCCTAACTCCCTGT
AATTTTCTATGTTCTTCTGCGCTAATAGGTCCGACATACCCAACAAATCAGCTACTG
TGCGCCCTTCAGGATAATGTCTGCGAACGAAGATTCGACATGCAATCCTGGCCAATCC
TTCTCCAGATCTTGAGCCTTAAAAAAGTACGCTCAGATACATTAGGTCTGAAGGATGT
AAGGTACAGACCCTAATACAGAAGCTTTGGCATGGATCGTATCTTCAACGAAATCACGG
TCCATATGCAGCTCTTGAGCCAAAAATCTTGCAAATTTTTAATGTAATCCTTACGAA
CAGGAACAAGCCTCTTATTCCCTTGCTCATCTGTATGCCAAACACGCGTCGGAATATCA
CGTATCGCTCGATAAGAGATCCCCACATTATATTGTAAAACGTTTCTGCCAGCGTTTT
ACCAAAACGATCACATACTCCTGCGGATCACAATGCTCAGGAACAGCAACATGCCATATACGC
GACGATAAGCTTCCTTCTTTCTCATGCTGCACAACAAGTAGTCTGTTAGCCTTTTCTGG
AAAGTGATGATAGACAAAGCAATAATAAATCCCACAAGTAGTCTGTTAGCCTTTTCTGG
CACAGAAAGTGGGGTGCGTCGTTTTCATATATGGTTAGTTAATCTGTTTTAT
TGGTCGACGTTTAAAAACACTTTCTTGTAGTAATAAAACGATTCTATCAAAACAA
ATTCTTAGATTTCTTACAAAAATCTCCTCTTTTCTTTTAGCCAAACCCCATCTTCGA
GCTATTCCAAACACAAACTCAAAAACCCTCTAGGTTTTGGAATTAACAACTCATAAAATTGAACT
GTTTTGTAATTAACTCAAAGCGATTTTTTCGCAAAAACCAAGAACTCAACATATTGCCAATATGGC
TTTGCTCTCGGTTTCAGAGCGATTTTTCTCTGCTTTATCGCTAAATCAGGAGGCGCTTAAGGGCTCT
AGATATACAAAAATGGCTCTCTGCTTTCTTATCTTCTTTACGAGAATAAGAAATTTTGTTATGGCT
TCCTGGGACGAACGTTTTCTCGATGTTCTCGATTAAGGCTGCTTTTACTTGCAAGACATTCCTCAG
CGAGCATTGAACGACATGTTCTCGATTAAGGCTGCTTTTACTTGCAAGACATTCCTCAG
GCCATTAATTGCTACAGGACATCTTGTCTGGCTTTAACTAGGACCAGTGCCGCCAGAA
```

FIG. 2B

```
AAAGATAGCGAGCACAAAGAGAGCTAATTATACAATTTAGAGGTAAGA
                                                    1
                                                  Met Lys
                                                  ATG AAA
                 10
Lys Leu Lys Ser Val Leu Val Phe Ala Ala Leu Ser Ser Ala
AAA CTC TTG AAA TCG GTA TTA GTG TTT GCC GCT TTG AGT TCT GCT
         20                                   30
Ser Ser Leu Gln Ala Leu Pro Val Gly Asn Pro Ala Glu Pro Ser
TCC TCC TTG CAA GCT CTG CCT GTG GGG AAT CCT GCT GAA CCA AGC
                                  40
Leu Met Ile Asp Gly Ile Leu Trp Glu Gly Phe Gly Gly Asp Pro
CTT ATG ATC GAC GGA ATT CTA TGG GAA GGT TTC GGC GGA GAT CCT
         50                                   60
Cys Asp Pro Cys Thr Thr Asp Phe Val Ala Ile Ser Met Arg Met
TGC GAT CCT TGC ACC ACT GAC TTT GTT GCT ATC AGC ATG CGT ATG
Gly Tyr Tyr Gly Tyr Asp Phe Val Gly Val Leu Gln Thr Asp
GGT TAT TAT GGT GAC TTT GTT GGT GTT CAA ACA GAT
                                  70
                                                     90
Val Asn Lys Glu Phe Gln Met Gly Ala Lys Pro Thr Thr Ala Thr
GTG AAT AAA GAA TTC CAA ATG GGT GCC AAG CCT ACA ACT GCT ACA
                                  100                120
Gly Asn Ala Ala Ala Pro Ser Thr Cys Thr Ala Arg Glu Asn Pro
GGC AAT GCA GCT GCT CCA TCC ACT TGT ACA GCA AGA GAG AAT CCT
         110
Ala Tyr Gly Arg His Met Gln Asp Ala Glu Met Phe Thr Asn Ala
GCT TAC GGC CGA CAT ATG CAG GAT GCT GAG ATG TTT ACA AAT GCT
                                  130
Ala Tyr Met Ala Leu Asn Ile Trp Asp Arg Phe Asp Val Phe Cys
GCT TAC ATG GCA TTG AAT ATT TGG GAT CGT TTT GAT GTA TTC TGT
```

FIG. 2C

```
                            140                     150
Thr Leu Gly Ala Thr Ser Gly Tyr Leu Lys Gly Asn Ser Ala Ser
ACA TTA GGA GCC ACC AGT GGA TAT CTT AAA GGA AAT TCA GCA TCT
                                  160
Phe Asn Leu Val Gly Leu Phe Gly Asp Asn Glu Asn His Ala Thr
TTC AAC TTA GTT GGC TTA TTC GGA GAT AAT GAG AAC CAT GCT ACA
        170                                             180
Val Ser Asp Ser Lys Leu Val Pro Asn Met Ser Leu Asp Gln Ser
GTT TCA GAT AGT AAG CTT GTA CCA AAT ATG AGC TTA GAT CAA TCT
                                  190
Val Val Glu Leu Tyr Thr Asp Thr Phe Thr Ala Trp Ser Ala Gly
GTT GTT GAG TTG TAT ACA GAT ACT TTT ACT GCT TGG AGT GCT GGA
        200                                             210
Ala Arg Ala Leu Trp Glu Cys Gly Cys Ala Thr Leu Gly Ala
GCT CGT GCA TTG TGG GAA TGT GGA TGC GCG ACT TTA GGC GCT
                                  220
Ser Phe Gln Tyr Ala Gln Ser Pro Lys Val Glu Glu Leu Asn
TCT TTC CAA TAC GCT CAA TCC AAG GTC GAA GAA TTA AAC
        230                                             240
Val Leu Cys Asn Ala Ala Glu Phe Thr Ile Asn Lys Pro Lys Gly
GTT CTC TGT AAC GCA GCT GAG TTT ACT ATC AAT AAG CCT AAA GGA
Tyr Val Gly Gln Glu Phe Pro Leu Asp Ala Ser Ile Asp Lys Lys Ala Gly Thr Asp
TAT GTA GGG CAA GAA TTC CCT CTT GAT GCC TCT ATT GAT AAA GCA GGA ACA GAT
        260                                             270
Gly Val Thr Gly Thr Lys Asp Ser Ile Asp Tyr His Glu Trp
GGT GTG ACA GGA ACT AAG GAT TCT ATT GAT TAC CAT GAA TGG

Gln Ala Ser Leu Ala Leu Ser Arg Leu Asn Met Phe Thr Pro
CAA GCA AGT TTA GCT CTC TCT AGA CTG AAT ATG TTC ACT CCC
```

FIG. 2D

| | | | | | | | | | | |
|---|---|---|---|---|---|---|---|---|---|---|
|Tyr|Ile|Gly|Val|Lys|Trp|Ser|Arg|Ala|Ser|Phe|Asp|Ala|Asp|Thr
TAC|ATT|GGA|GTT|AAA|TGG|TCT|CGA|GCA|AGT|TTT|GAT|GCA|GAC|ACG 290 300

Ile Arg Ile Ala Gln Pro Lys Ser Ala Thr Thr Val Phe Asp Val
ATT CGT ATT GCT CAG CCG AAG TCA GCT ACA ACT GTC TTT GAT GTT
310 320 330

Thr Thr Leu Asn Pro Thr Ile Ala Gly Ala Gly Ala Asp Lys Ala
ACC ACT CTG AAC CCA ACT ATT GCT GGA GCT GAT AAA GCT

Ser Ala Glu Gly Gly Gln Leu Gly Thr Met Gln Ile Val Ser Leu
AGC GCA GAG GGT CAG CTC GGA GAT ACC ATG CAA ATC GTT TCC TTG
340

Gln Leu Asn Lys Met Lys Ser Arg Lys Ser Cys Gly Ile Ala Val
CAA TTG AAC AAG ATG AAA TCT AGA AAA TCT TGC GGT ATT GCA GTA
350 360

Gly Thr Thr Ile Val Asp Ala Asp Tyr Ala Val Thr Val Glu
GGA ACA ACT ATT GTG GAT GCA GAC TAC AAA GCA GTT ACA GTT GAG
370

Thr Arg Leu Ile Asp Glu Arg Ala Ala His Val Asn Ala Gln Phe
ACT CGC TTG ATC GAT GAG AGA GCT CAC GTA AAT GCA CAA TTC
380 390

Arg Phe OC
CGC TTC TAA TTAATTGTATAATTTGTTAAACTTTGGCAAGTTTATCTTTGTTAATA
394

ACGTTAATAACACTATCCGTGTTTCTGGGCTCGACTTCGGTCGGGTCCAGTTTTTTTGC
AAAATTTTTTTCTTACTTTCGATCTCCCTCCTATCTCTCTTACAACAAAATCTAAAAT
TTCTCTAAAGAAGATTGCATAAAAGGCCTCTTTCCAGTACTACTATATCGGTCTACTTGAGC
GCGCCCGTAGCTCAATGGTAGAGCTGTAGCCTTCCAAGCTGTACCGGTGTCAGTTCGATTCT
GATCGGGCTCTTTTTTACTCCTGTATGACTCCCAAGTCTGAAATCTGAGCGTCTCTCAGA

FIG. 2E

TGCCTTGTTAACACATAAAAAGAGGAGGAACAAAGCTTGGAACTTTCCTGCAAACTCACTTTA
AAAGAACTATTAGAATCCGGGGCACATTTTGGACACCAGACAAGTCGCTGGAATCCCAAG
ATGAAGCCTTTTATTTTTGAAGAAAAAATGGCCTTTACATCATCGACTTGGCTAAAACT
TTAGGTCAGTTGAAAAAGGCTGTTTCTTGCATTCAAAAAACTATCGATCAAGAGAGGTCT
ATTTTTGTTTGTTGGAACAAAAAAACAAGCAAAAACAGATCATTAGAGAAGCTGTATCGA
ATGTGGCGAATTC

CHLAMYDIA MAJOR OUTER MEMBRANE PROTEIN

This application is a divisional of Ser. No. 08/144,095, filed Oct. 28, 1993 now abandoned, which is a continuation of Ser. No. 07/691,639, filed Apr. 25, 1991 now abandoned, which is a continuation of Ser. No. 06/818,523, filed Jan. 13, 1986 now abandoned, which is a continuation-in-part of Ser. No. 06/692,001, filed Jan. 14, 1985, now abandoned, each of which are incorporated herein by reference.

BACKGROUND OF THE INVENTION

1. Field of the Invention

*Chlamydia trachomatis* is a major human pathogen responsible for such diseases as trachoma, inclusion conjunctivitis, pneumonia, lymphogranuloma venereum, and mucous membrane genital tract infections such as cervicitis and urethritis. The latter infections may develop systemic complications resulting in epididymitis, salpingitis, or perihepatitis. Thus, it would be of great medical interest to develop reagents and vaccines useful in the diagnosis and treatment of patients infected with *Chlamydia trachomatis*.

*Chlamydia trachomatis* species are divided into two biovars, the trachoma biovar and the lymphogranuloma venereum (LGV) biovar, based on the disease inducing characteristics of the species. Each biovar, in turn, includes a number of serovars based on specific serological determinants. The trachoma biovar contains twelve known serovars, while the LGV biovar includes three known serovars. Unique serological determinants which are characteristic of the species, biovar, and serovar have been associated with the major outer membrane protein (MOMP), which protein accounts for over 60% of the total cell wall protein synthesized during chlamydial development. The major outer membrane protein of each serovar appears to have a unique structure and includes species-specific, biovar-specific, and serovar-specific epitopes, allowing *Chlamydia trachomatis* to be classified by reaction with a panel of monoclonal antibodies specific for the various epitopes. The molecular weight of the various MOMP's generally ranges from about 38 kD to 45 kD. The serovars display varying antigenic complexity, with certain serovars eliciting broad cross-reactivity with others in the same biovar, while other serovars display little or no such cross-reactivity.

Vaccines utilizing purified and unpurified preparations of intact *Chlamydia trachomatis* have been prepared and tested on monkeys. While successful protection against subsequent challenge with the same chlamydial serovar was achieved, it was found that heterologous serovar challenge resulted in more severe pathology than that experienced by controls who had not been immunized. In human trials, immunization with the vaccines afforded significant protection against the serovar of the vaccine for up to two years, but hypersensitivity resulted from infection with heterologous serovars.

2. Description of the Relevant Art

The nature of the major outer membrane protein and its relation to the biovars and serovars of *Chlamydia trachomatis* are discussed in Grayston and Wang (1975) J. Infect. Dis. 132:87–105; Stephens et al. (1982) J. Immunol. 128:1083–1089; and Caldwell et al. (1981) Infect. Immun. 31:1161–1176. Inhibition of infectivity of *Chlamydia trachomatis* by both anti-chlamydial antisera and monoclonal antibodies has been demonstrated. Caldwell and Perry (1982) Infect. Immun. 38:745–754; and Clark et al. (1982) Infect. Immun. 38:1273–1278. Vaccine trials conducted with intact chlamydial elementary bodies are reported by Collier (1961) Lancet 1:795–800; Wang et al. (1967) Amer. J. Ophthal. 63:1615–1630; and Woolridge et al. (1967) Amer. J. Ophthal. 63:1645–1653. The cloning and expression of a gene encoding a 74,000 dalton chlamydial antigen in *E. coli* is reported by Stephens et al. (1983) Abstracts Annual Meeting American Society of Microbiology, B29, p. 35. Stephens et al. failed to obtain expression of a major outer membrane protein. Wenman and Lovett (1982) Nature 296:68–70, report the expression of a 19,000 dalton *Chlamydia trachomatis* polypeptide. The polypeptide does not appear to be involved in the major outer membrane protein. Allan et al. (1984) Infect. Immun. 45:637–641, recently reported the cloning of the major outer membrane protein gene. Nano et al. (1985) Infec. Immun. 45:637–641 report the sequencing of the first 25 N-terminal amino acids of the major outer membrane protein and the cloning of at least a portion of the gene. An immunoassay for the detection of *Chlamydia trachomatis* antigen is described in U.S. Pat. No. 4,497,899.

SUMMARY OF THE INVENTION

Polypeptide compositions having immunological activity corresponding to that of a major outer membrane protein (MOMP) of *Chlamydia trachomatis* are produced by expressing a chimeric DNA construct comprising a polynucleotide encoding at least a portion of the MOMP under the regulatory control of a regulatory system recognized by a unicellular expression host. The MOMP polynucleotide may code for the entire protein or for a fragment thereof, and may be expressed in conjunction with another structural gene to yield a fused translation product. Such polypeptide compositions will be characterized by the presence of non-interfering amounts of substances derived from the expression, which presence may be used to distinguish the polypeptides of the present invention from the natural polypeptides. The polypeptide compositions of the present invention are useful as substitutes for the naturally-occurring MOMP's of *Chlamydia trachomatis*, particularly as immunological reagents, e.g., in serological assays to detect the presence of antibodies in blood, the immunogenic substance in vaccines, and the like. The MOMP polynucleotides will also be useful as labelled probes for diagnostics.

BRIEF DESCRIPTION OF THE DRAWINGS

FIG. 1 depicts the sequence of inserted DNA and its restriction sites for the vector λgt11/L2/33; and FIG. 2 depicts the DNA sequence and amino acid sequence for the MOMP $L_2$ serovar.

DESCRIPTION OF THE SPECIFIC EMBODIMENTS

Methods and compositions are provided for the efficient expression of polypeptides demonstrating immunological activity analogous to that of a major outer membrane protein (MOMP) of *Chlamydia trachomatis*. By analogous immunological activity, it is meant that, when administered to a vertebrate, the polypeptides will elicit an immunological response which is cross-reactive with antibodies elicited by administration of the natural MOMP. The present invention employs a DNA construct including a MOMP polynucleotide or fragment thereof encoding a polypeptide under the transcriptional and translational control of suitable regulatory sequences. MOMP polypeptides free from other chlamydial antigens are obtained by expressing the MOMP polynucleotides in a unicellular host other than *Chlamydia trachomatis*.

The MOMP polynucleotides of the present invention may be initially derived from any of the chlamydial serovars and may be employed in a natural or modified form. MOMP nucleotides having a sequence corresponding to an intact natural MOMP gene will usually be employed when it is desired to express the entire MOMP, although it will be possible to alter the sequence for a desired purpose, e.g., to conform to the codon bias of the expression host (as discussed below), or to create or delete restriction sites, so long as the amino acid sequence is not significantly altered. Shorter DNA sequences corresponding to portions of the MOMP gene will be employed when it is desired to produce only a fragment of the natural proteins. Usually, such sequences will encode for an epitopic region(s), comprising at least 27 bp, usually at least 36 bp, preferably at least 45 bp, and may be much longer.

It will sometimes be desirable to express the MOMP polynucleotide together with other gene(s) in order to provide fused translation products having desirable properties. For example, when producing low molecular weight MOMP polypeptide fragments (below about 5 kD), it may be desirable to fuse the MOMP polypeptide to an immunogenic carrier, e.g., tetanus toxoid or hepatitis B surface antigen. It is also possible to fuse MOMP fragments from more than one serovar to each other and/or a gene expressing a suitable immunogenic carrier. Conveniently, the MOMP polynucleotide will be inserted in proper reading frame with the fused gene and under the regulatory control of the regulatory system of the fused gene. Recovery of the gene product may be facilitated by employing a secretory protein as the fused gene product, as described below.

The MOMP polypeptides may be glycosylated, partially glycosylated, or unglycosylated, depending on the nature of the expression host. Generally, prokaryotes such as *E. coli* will provide no glycosylation of the translated MOMP gene products, while yeast and mammalian cell culture will provide partial or substantial glycosylation. Thus, it will be possible to vary the final MOMP product by appropriate selection of the expression host.

The MOMP polynucleotide may be synthetic or natural, or combinations thereof. A natural MOMP gene (or a portion thereof) may be obtained by preparing a *Chlamydia trachomatis* genomic library and screening for the presence of the MOMP gene. Screening may be accomplished using antibodies for the gene product or using labelled DNA probes specific for the polynucleotide. Both methods are exemplifed in the Experimental section hereinafter. Suitable antibodies are commercially available or may be prepared from purified MOMP obtained from *Chlamydia trachomatis* by well known techniques. Suitable DNA probes may be obtained based on the amino acid sequence of the MOMP, or based on the polynucleotide sequence which is reported hereinafter for the MOMP of the $L_2$ serovar (see FIG. 2). Conveniently, the λgt11/L2/33 clone which has been deposited in connection with this patent application may be labelled and used as a screening probe. A specific method for selecting a clone expressing the MOMP of the $L_2$ serovar from a *Chlamydia trachomatis* genomic library is set forth in the Experimental section hereinafter. This method can be modified to allow for selection of MOMP gene(s) from other serovars.

Synthetic polynucleotide sequences encoding for at least a portion of the MOMP gene of *Chlamydia trachomatis* may also find use, either alone or in combination with the naturally-occurring sequences. Coding for the synthetic sequences may be based on either the reported amino acid sequences for the MOMP's or on the polynucleotide sequences which are determined from the MOMP genes by known techniques. When used for preparing polypeptides as immunological reagents or as vaccines, it is usually desirable that the synthetic nucleotide fragment code for an oligopeptide corresponding to an epitopic site of the natural MOMP. Often, such epitopic sites may be inferred from the folding rules of Chou and Fasman (1974) Biochemistry 13:211–222, in conjunction with an analysis of hydrophobic and hydrophilic regions of the protein as taught by Hopp and Woods (1981) Proc. Natl. Acad. Sci. USA 78:3824–3828. Alternatively, the DNA sequences encoding the polypeptide regions which react with particular monoclonal antibodies may be identified by the high-density phage procedure described by Nunberg et al. (1984) Proc. Natl. Acad. Sci. USA 81:3675–3679. The oligopeptide may then be screened for eliciting Ab cross-reactive with the naturally-occuring MOMP.

A number of techniques are available for synthesizing short, single-stranded DNA fragments, e.g., the phosphoramidite method described by Beaucage and Carruthers (1981) Tetrahedron Lett. 22:1859–1862. A particularly useful adaptation of the method of Beaucage and Carruthers is reported by Warner et al. (1984) DNA 3:401–411. Using the method of Urdea et al., single-stranded DNA fragments having a length of up to 100 bases may be synthesized, and double-stranded DNA fragments may be formed by annealing and ligating a plurality of single-stranded fragments under appropriate conditions. Alternatively, the complementary strand may be added using DNA polymerase with an appropriate primer sequence.

When preparing synthetic MOMP polynucleotides, it may sometimes be desirable to modify the natural nucleotide sequence. For example, it will often be preferred to use codons which are preferentially recognized by the desired host. When employing a yeast host, codons which appear at high frequency in the structural genes encoding the yeast glycolytic enzymes may be employed. In some instances, it may be desirable to further alter the nucleotide sequence to create or remove restriction sites to increase stability or to substitute one or more amino acids in the resulting polypeptide. Such changes may be made to enhance the immunogenicity of the polypeptide, facilitate conjugating the polypeptide to a carrier protein, or the like. It may also be desirable to add amino acids to the N-terminus or C-terminus of the polypeptide, where such additional amino acids provide for a desired result.

To produce a desired MOMP polypeptide, the MOMP polynucleotides will be incorporated into DNA constructs capable of being introduced into a desired expression host, usually either a prokaryotic host or eukaryotic host, such as yeast. Such DNA constructs will include the MOMP polynucleotide encoding the polypeptide product, transcriptional and translational initiation regulatory sequences joined to the 5'-end of the polynucleotide, and transcriptional and translational termination regulatory sequences joined to the 3'-end of the polynucleotide. The DNA constructs will usually also include a replication system recognized by the expression host to allow for self-replication, and will often include other functional sequences such as markers allowing for selection of transformed hosts, additional replication systems, secretory leader and processing signal sequences, and the like. The replication system, however, is not necessary since the DNA construct may allow for integration into the host genome. Integration is facilitated by providing short DNA fragments on either side of the MOMP polynucleotide, which fragments are homologous to a desired location in the host genome.

The transcriptional initiation regulatory sequences will include a promoter region recognized by the expression host. For *E. coli* hosts, the lac promoter, lambda $P_L$ or $P_R$, or the β-galactosidase promoter, as exemplified in the Experimental section hereinafter, are suitable. For yeast hosts, suitable promoters include those involved with the enzymes in a yeast glycolytic pathway, such as the promoters for alcohol dehydrogenase, glyceraldehyde-3-phosphate dehydrogenase, pyruvate kinase, triose phosphate isomerase, phosphoglucoisomerase, phosphofructokinase, and the like. By employing these promoters with other regulatory sequences, such as enhancers, operators, and the like, and using a host having an intact regulatory system, one can regulate the expression of the MOMP polypeptide by a number of techniques, such as varying the carbon source, e.g., replacing glucose with galactose; varying the concentration of a nutrient, e.g., acid phosphatase, or changing the temperature with a temperature sensitive promoter or regulatory system.

The transcriptional termination regulatory sequence will include a terminator, preferably a terminator balanced with the promoter to provide proper transcription. Conveniently, the terminator which is naturally found with the promoter may be employed. In the exemplary embodiment described in the Experimental section hereinafter, the MOMP polynucleotide is inserted between the β-galactosidase promoter and terminator within the β-galactosidase structural gene so that a fusion product is formed.

Enhanced yields of the polypeptides of the present invention may be obtained by employing DNA constructs which include a secretory leader and processing signal sequence to effect secretion of the gene product in yeast. The use of such secretory leader and processing signal sequences will be particularly effective with polypeptides below about 40 kilodaltons, more usually below about 30 kilodaltons, although it is expected that the system will function with polypeptides equal to the length of the whole MOMP, i.e., ranging from 38 to 45 kilodaltons. The secretory leader and processing signal sequences will normally be derived from naturally-occurring DNA sequences in yeast which provide for secretion of a polypeptide. Such polypeptides which are naturally secreted by yeast include α-factor, a-factor, acid phosphatase, and the like. If desired, the naturally-occurring sequence may be modified, for example, by reducing the number of lys-arg pairs in α-factor which define the processing site (while retaining at least one pair), or by reducing the length of the secretory leader sequence (while retaining sufficient length to provide for secretion) or by introducing point mutations, deletions or other modifications which facilitate manipulation, e.g., introducing restriction recognition sites. Conveniently, the secretory leader and processing signal sequence may be joined to the MOMP polynucleotide by providing appropriate cohesive ends on the polynucleotide fragment, by use of appropriate adaptor molecules, or a combination of both. A portion of the structural gene for the secretory protein may be left in the final DNA construct when it is desired to produce a fused translation product, as discussed above.

Polypeptides of the present invention may also be recovered intracellularly as follows. After the transformed cell culture has reached a high density, the cells will be separated, typically by centrifugation, lysed, and the MOMP polypeptides isolated and purified by various techniques, such as extraction, affinity chromatography, electrophoresis, dialysis, and combinations thereof.

The MOMP polypeptides may also be prepared by conventional solid-phase synthesis techniques, such as those described by Merrifield (1963) J. Am. Chem. Soc. 85:2149–2156. Such solid-phase techniques are suitable for preparation of polypeptide fragments of up to about 50 to 100 amino acids, or more. Generally, however, as the length of the polypeptide increases above 25 amino acids, the difficulty in the synthesis increases and the desirability of employing a solid-phase synthesis technique diminishes.

The polypeptides of the present invention, and fragments thereof, may be employed in a variety of ways. The polypeptides can be employed both as labelled and unlabelled reagents in various immunoassays, bioassays, and the like, for the detection of *Chlamydia trachomatis* or antibodies to *Chlamydia trachomatis* in a biological sample, e.g., serum. Suitable labels include radionuclides, enzymes, fluorescers, chemiluminescers, enzyme substrates or co-factors, enzyme inhibitors, particles, dyes, and the like. Such labelled reagents may be used in a variety of well known assays, such as radioimmunoassays, enzyme immunoassays, e.g., ELISA, fluorescent immunoassays, and the like. See, for example, U.S. Pat. Nos. 3,766,162; 3,791,932; 3,817,837; 3,996,345; and 4,233,402. Polypeptides of the present invention may also find use in vaccines against infection by *Chlamydia trachomatis*. Larger polypeptides, having a molecular weight exceeding about 5,000 daltons, may be used without further modification. Smaller haptens (i.e., those below about 5 kD), however, should be conjugated to an appropriate immunogenic carrier in order to elicit the desired immune response. Suitable immunogenic carriers include tetanus toxoid and hepatitis B surface antigen. It will be possible to link short DNA fragments expressing the MOMP polypeptides to genes expressing proteins from other pathogenic organisms or viruses. In this way, the resulting fused proteins may provide immunity against more than one disease.

In preparing a vaccine, the polypeptides will normally be incorporated in a physiologically acceptable medium, such as water, physiological saline, phosphate buffered saline, and the like. The vaccine may be administered intravenously, intraarterially, subcutaneously, intraperitoneally, or the like. The amount of immunogen employed per dose will be about 5 to 10 micrograms, if liquid, in a volume of about 0.25 to 1 ml, and may be administered repeatedly at about 2 to 4 week intervals, usually not more than 2 or 3 times.

The polynucleotides of the present invention may be employed as labelled polynucleotide probes suitable for screening biological samples for the presence of various strains of *Chlamydia trachomatis*. Probes comprising DNA or RNA from conserved regions of the MOMP gene may be employed for detecting a broad range of Chlamydia, while probes comprising regions of the MOMP gene specific for a particular strain may be employed to identify that strain. The polynucleotide sequences in such probes will typically be at least 12 nucleotides, more typically 16 or more nucleotides. Conveniently, the nucleotide fragment may be synthesized based on the sequence set forth in FIG. 1, hereinafter.

Suitable labels include radionuclides, heavy metals, organic ligands, and the like, which allow for detection in conventional assays. Biological samples will be prepared in a conventional manner, e.g., by lysing the Chlamydia to release the nucleic acids.

EXPERIMENTAL

The following experiments are offered by way of illustration, not by way of limitation.

MATERIALS AND METHODS

Reagents

DNase, RNase, endonuclease restriction enzymes, T4 ligase, kinase, DNA Polymerase I, and EcoRI methylase were obtained from Bethesda Research Laboratories. Nitrocellulose was obtained from Schleicher and Schuell. Peroxidase conjugated anti-mouse, anti-rabbit, and peroxidase anti-peroxidase (PAP) sera were obtained from Cappell. Proteinase K, isopropylthiogalactoside (IPTG), and 4-chloro-1-naphthol were from Sigma Chemical Co. Phage packaging mix was obtained from Arersham. CNBr-activated SEPHAROSE®-4B was obtained from Pharmacia.

Bacterial Strains

*E. coli* Y1088, Y1089, Y1090, and BNN 97 were obtained from R. Young and R. Davis (Stanford University). For *C. trachomatis*, two trachoma strains, B/TW-5/OT, and C/TW-3/OT, and one LGV strain, $L_2/434/Bu$, were grown in HeLa 229 cells and Renografin purified as described by Kuo et al. (1977) in: "Nongonococcal Urethritis and Related Infections," Hobson and Holmes, eds., Am. Soc. Microbiol. pp. 176–185.

Antibodies

Polyvalent antiserum to *C. trachomatis* was obtained from rabbits immunized with purified LGV ($L_2$ serovar) organisms that were grown in chick embryo yolk sacs. Anti-*E. coli* reactivities in this antiserum were removed by passage through a SEPHAROSE®-4B column derivitized with an *E. coli* lysate. For this purpose, approximately 20 mg of DNase and RNase treated lysate of induced BNN 97 were coupled to 1 mg of CNBr-activated SEPHAROSE®-4B according to the manufacturer's instructions. The development, specificities, and ascites production of monoclonal antibodies specific for *C. trachomatis* have been previously reported (Stephens et al. (1982) J. Immunol. 128:1083).

Insertion of Chlamydial DNA into λgt11

Chlamydial DNA was isolated from cell extracts of serovars $L_2$, B, and C by proteinase K treatment (65 μg/ml, 45° C., 1 hr.) and solubilization in 1% sodium dodecyl sulfate (SDS). Following phenol extraction, the preparations were treated with 50 μg/ml RNase (60° C., 30 min.), phenol/chloroform extracted, and ethanol precipitated. Standard procedures were used for enzymatic reactions and for isolation of λ phage DNA (*Molecular Cloning* Maniatis et al. Cold Springs Harbor Lab., 1982). Chlamydial DNA from serovar $L_2$ (150 μg) was partially digested with DNase I as previously described (Ruther et al. (1982) Proc. Natl. Acad. Sci. USA 79:6852). Digested DNA was fractionated in a 1.25% agarose gel, and 500–2000 base pair fractions were collected on Whatman DE-81 paper and eluted as previously described (Dretzen et al. (1981) Annals of Biochem. 112:295). After treatment with DNA polymerase I, the DNA was methylated with EcoRI methylase, and 2 μg of this preparation were ligated to phosphorylated EcoRI linkers with T4 ligase. These fragments were then cleaved with EcoRI endonuclease and fractionated on a SEPHAROSE® G-150 column. Chlamydial DNA fractions were pooled and ethanol precipitated, and 20 ng of the chlamydial DNA were ligated to 1 μg of EcoRI cleaved λgt11. The EcoRI site is located within the β-galactosidase gene under the regulatory control of the β-galactosidase promoter and terminator. The ligated DNA was packaged into phage according to the manufacturer's instructions. Phage were plated and amplified in *E. coli* Y1088, and approximately $2 \times 10^5$ recombinant phages were obtained.

Screening of Recombinant Phages

*E. coli* Y1090 was infected with recombinant phage preparations that resulted in approximately $10^4$ plaque forming units (PFU) per 150 mm plate. Plates were initially incubated at 42° C. until small plaques became visible (approx. 5 hrs.). Plates were then overlayed with IPTG saturated nitrocellulose disks and incubated an additional 2 hrs. at 37° C. The nitrocellulose disks were carefully removed from the plates, rinsed in phosphate buffered saline (PBS) (pH 7.4) to remove any residual agar, and blocked in PBS containing 5% bovine serum albumin (BSA) for 60 min. at 37° C. to prevent subsequent nonspecific adsorption of protein. The disks were incubated with monoclonal antibodies (1:1000 dilution in PBS containing 0.05% TWEEN®-20, detergent) for 2 hr., at room temperature or overnight at 4° C. The disks were washed for 1 hr. with 6 changes of PBS-TWEEN®, detergent and incubated with peroxidase-conjugated, anti-mouse antibody (1:2000) for 1 hr. at room temperature, followed by a 1 hr. incubation with peroxidase anti-peroxidase (PAP) (1:2000 dilution). The disks were then washed with 6 changes of PBS-TWEEN®, detergent, followed by 2 changes of PBS. The immune reactions were detected by adding 0.5 mg/ml of 4-chloro-1-naphthol and 0.001% $H_2O_2$ in PBS and agitated for 5–15 min. Plaques showing positive reactions were selected, plated at low densities, and reassayed with antibody. This process was repeated until all plaques were reactive.

Analysis of Proteins by SDS-PAGE and Immunoblotting

Lysogens were produced from selected λgt11 recombinants by infecting *E. coli* Y1089 as previously described by Young and Davis (1983) Proc. Natl. Acad. Sci. USA 80:1194. Lysates from induced recombinant lysogens were prepared, and 20 μg aliquots were electrophoresed on 7.5% or 10% SDS-polyacrylamide gels (SDS-PAGE) according to Laemmli (1970) Nature 227:680. The proteins in some gels were stained with Coomassie brilliant blue, while those from other gels were electrophoretically transferred to nitrocellulose for immunoblotting, as described by Towbin (1979) Proc. Natl. Acac. Sci. USA 76:4350–4354. Following electrophoretic transfer, nitrocellulose sheets were blocked in 5% BSA and probed with either a 1:1000 dilution of rabbit polyvalent anti-*C. trachomatis* antiserum or mouse ascites containing high titered monoclonal antibody. Immune reactions were detected as described above for the screening of recombinant plaques, except that the PAP step was omitted. Prestained molecular weight standards were: myosin (200,000), phosphorylase B (92,500), BSA (68,000), ovalbumin (43,000), chymotrypsinogen (25,700), lactoglobulin (18,400), and cytochrome C (12,300) (Bethesda Research Laboratories).

Characterization of λgt11/L2/33 Insert DNA

λgt11/L2/33 insert DNA was obtained from EcoRI digests of the recombinant phage and separated on agarose gels. For dot blot hybridization, $^{32}$P-labelled insert DNA was reacted with lysates of *C. trachomatis* serovars A/G-17/OT, B/TW-5/OT, Ba/AP-2/OT, C/TW-3/OT, D/UW-3/Cx, E/UW-5/Cx, F/UW-6/Cx, G/UW-57, H/UW-43/Cx, I/UW-12/Ur, J/UW-36/Cx, K/UW-53/Cx, $L_1/440/Bu$, $L_2/434/Bu$, $L_3/404/Bu$, *C. psittaci* strain Mn, and HeLa 229 host cells. Lysates were prepared from approximately 10 μg of each chlamydial strain by proteinase K digestion (1 mg/ml in 10 mM Tris, pH 8.5, and 1 mM EDTA) for 1.5 hr. at 37° C. Samples were made to 0.2N NaOH, heated to 100° C. for 5 min., and placed on ice. The NaOH was neutralized with one volume of cold 0.2M acetic acid, followed by 0.5 volume of cold 20×SSC. The samples were filtered through nitrocellulose sheets and the sheets were washed with 6×SSC, air dried and baked 3 hr. at 80° C. The sheets were probed with $^{32}$P-labelled λgt11/L2/33 insert at 65° C. by standard procedures (*Molecular Cloning* supra.) Southern blots of BamHI-digested *C. trachomatis* DNA and endonuclease restriction mapping of the λgt11/L2/33 insert were performed by standard procedures (*Molecular Cloning* supra.).

Insertion of Chlamydial DNA into λ 1059

A library of chlamydial genomic DNA was produced in the bacteriophage lambda 1059 system, which cloning system was described by Karn et al. (1980) Proc. Natl. Acad. Sci. USA 77:5172–5176. *C. trachomatis* $L_2$ DNA was randomized by partial digestion with endonuclease restriction enzyme Sau3A or cleaved with BamHI and ligated to BamHI digested vector. Ligated DNA was packaged in vitro, as described by Sternberg et al. (1977) Gene 1:255–280, and plated in *E. coli* Q359 for screening as described in Karn et al. (1980) suora. Phages were plated in *E. coli* Q359 at densities of approximately $3 \times 10^3$ plaque forming units per 150 mm plate. The plates were overlayed with nitrocellulose disks and the disks containing plaque adsorbed DNA were air dried and baked 3 hr at 80° C. The disks were probed with $^{32}$P labelled λgt11/L2/33 insert DNA at 60° C. by standard procedures (*Molecular Cloning*, supra). Several plaques that produced strong signals were picked and reassayed as above until all plaques from a clone were uniformly reactive. DNA was isolated from the selected phage recombinants by standard procedures (*Molecular Cloning*, supra). Two clones were mapped by endonuclease restriction analysis and Southern blotting by standard procedures (*Molecular Cloning*, supra). Both λ1059 recombinants had more than one BamHI insert, however, bands with identical gel mobilities were identified which were not shared with bands from the vector, and some of these bands hybridized to the insert DNA probes in Southern blots. This process permitted mapping of contiguous endonuclease restriction sites that flanked the location of the homolog to the λgt11/L2/33 insert. The map obtained by endonuclease restriction analyses was verified by generating subclones of specific fragments in a plasmid vector (pUC 18), and predicted cross-hybridizations between these clones and with the λ1059 recombinants were observed in Southern blots. Fragments that included the putative coding region and flanking regions were used for DNA sequencing.

RESULTS

Detection of Chlamydial Antigens

DNA obtained from *C. trachomatis* serovar $L_2$ was partially digested with DNase I and inserted into the bacteriophage vector λgt11. The resulting plaques were transferred to nitrocellulose for the direct detection of *C. trachomatis*-specific antigens. Polyvalent anti-$L_2$ rabbit serum detected seven plaques that produced strong immune reactions from among the $2 \times 10^4$ recombinant plaques assayed. The positive plaques were replated at low densities and screened with polyvalent antiserum.

After plaque purification, the seven recombinants were tested with a pool of monoclonal antibodies. The monoclonal antibody pool consisted of four antibodies (2C1, 2G1, 2H2, AE11) that each bind a mutually exclusive MOMP determinant (Stephens et al. (1982) supra.) One of the clones, designated λgt11/L2/33, reacted with the pool of antibodies, while the other six recombinant clones did not. Subsequently, λgt11/L2/33 was tested with each of over 15 monoclonal antibodies representing species-, subspecies-, and type-specific anti-chlamydial reaction patterns. The specificities of the antibodies and their reaction pattern with λgt/11/L2/33 are presented in Table 1. The reaction pattern demonstrated that λgt11/L2/33 was producing a polypeptide that displays species-, subspecies-, and type-specific epitopes of the chlamydial MOMP. The lack of reaction of λgt11/L2/33 to antibodies not reactive with the $L_2$ serovar was expected since the recombinant was derived from serovar $L_2$ DNA. Two antibodies (AE11 and 3H10) that do react with native $L_2$ MOMP did not react with the polypeptide expressed by λgt11/L2/33 using this plaque assay. The two antibodies, however, gave positive reactions with λgt11/L2/33 expressed polypeptide in immunoblotting.

TABLE 1

| Monoclonal Antibody No. | Serovar Specificities | Reaction with λgt11/L2/33 |
| --- | --- | --- |
| 2C1, IH8 | all serovars | +* |
| AE11 | all serovars except C | −* |
| 3H10 | A,B,D,E,F,G,H,K,L1,L2,L3 | −* |
| KG5 | B,D,E,F,G,H,K,L1,L2,L3 | + |
| DA10 | B,D,E,G,F,L1,L2,L3 | + |
| 2G3 | B,D,E,K,L1,L2,L3 | + |
| 2G1 | B,F,G,H,K,L2,L3 | + |
| 3H1, 2IIE3 | B,D,E,L1,L2 | + |
| JC8 | B,D,G,F,L2 | + |
| FE10 | E,G,F,L2 | + |
| JG1 | B,D,E,L2 | + |
| 2H2, 2H5 | L2 | + |
| 1B7, DD1 | B | − |
| 2B1 | C,J | − |
| FC2 | F | − |
| JG9 | D | − |

*Positive reaction obtained by immmunoblotting.

Analysis of Recombinant Fusion Polypeptides

*E. coli* lysogens were prepared for each of the positive λgt11 clones to provide a source of fusion polypeptides for analysis. Lysates obtained from induced lysogens were assessed by Coomassie blue stained PAGE gels and by immunoblotting of the proteins that were electrophoretically transferred from PAGE gels to nitrocellulose. The molecular weights of these fusion proteins were estimated to range from 132,000 to 146,000.

Immunoblot analysis of PAGE gels using polyvalent rabbit anti-$L_2$ revealed that each of the seven clones produced strong reactions in the plaque assay. The λgt11/L2/33 product stained most intensely, while the products from two other recombinants stained very faintly. Immunoblot analysis was also performed with the monoclonal antibodies. Of the seven recombinants, only λgt11/L2/33 reacted with monoclonal antibodies as expected from the results on the plaque assays with these same antibodies. The monoclonal antibodies that recognized species-specific and subspecies-specific determinants on $L_2$ chlamydial MOMP reacted strongly with the polypeptide produced by λgt11/L2/33, while the $L_2$ type-specific monoclonal antibodies produced negative or equivocal reactions.

Characterization of λgt11/L2/33 Insert DNA

DNA from the λgt11/L2/33 recombinant was isolated, labelled with $^{32}$P, and used to probe dot blots of each of the 15 *C. trachomatis* serovars, the Mn strain of *C. psittaci*, and HeLa 229 host cells. Reactions were detected with all chlamydiae but not with HeLa 229 host cell DNA. Furthermore, Southern blots of BamHI digests of *C. trachomatis* DNA obtained from serovars $L_2$, B, and C revealed one fragment in each preparation which reacted with $^{32}$P-labelled insert DNA from λgt11/L2/33. The molecular weight of this fragment varied slightly between serovars but was approximately 9.4 kb.

Preparations of λgt11/L2/33 insert DNA were obtained from EcoRI digests and separated on agarose gels. The insert was estimated to be about 1.1 kb in length with restriction sites for HaeII, HaeIII, HhaI, and XhoI. Restriction sites for AccI, BamHI, BclI, BstEII, EcoRI, EcoRV, PstI, PvuI, SstI, and SstII were not detected.

The approximately 1.1 kb insert DNA was sequenced by standard techniques, and the sequence is set forth in FIG. 1.

Sequencing of λ1059 Inserts

Lambda 1059 recombinants having 9.2 to 9.8 kb inserts that were shown to be homologous with λgt11/L2/33 by Southern analysis were used for endonuclease restriction mapping, and additional Southern analyses. Two contiguous fragments (BamHI/EcoRI and EcoRI/EcoRI) were identified, and these contain sufficient base pairs to encode for the $L_2$ MOMP gene product. These fragments were cloned into M13 for DNA sequencing. The sequence data for a 9.2 kb fragment (designated L2 B9-F DNA) are set forth in FIG. 2.

The sequence includes an untranslated region comprising 1287 bases, followed by a 66 base region encoding a 22 amino acid leader sequence. Coding for the MOMP begins at base 67 (amino acid 23) and extends through base number 1182 (amino acid 394). The molecular weight for the MOMP including the leader is calculated to be 42,557 daltons.

The N-terminus of the MOMP was located on the basis of the 25 amino acid N-terminus reported by Nano et al. (1985) supra. Differences in the sequences of the N-terminus reported by Nano et al. and that reported herein are found at amino acid residues 32, 44, and 45, as numbered in FIG. 2. These differences may result from differences among the isolates or mistakes in amino acid sequencing.

The sequence set forth in FIG. 1 corresponds to amino acids 247 through the 3'-terminus in FIG. 2, with certain deviations. Bases 36–38 in FIG. 1 are AGA, corresponding to amino acids GlyGlu, while bases 773–775 in FIG. 2 are TGT, corresponding to amino acids GlyVal. These deviations are underlined in both Figures. The DNA sequence corresponding to amino acids 305 through 394 in FIG. 2 has several deviations from FIG. 1 which result in a different reading frame for the sequence of FIG. 2. Base numbers 174, 181, and 186 in FIG. 1 were not detected in the λ 1059 clones. Base number 35 in FIG. 1 is a T, while the corresponding base in FIG. 2 (in amino acid 357) is a C. Finally, a G is inserted in amino acid 358 and a G is inserted in amino acid 374 in the sequence of FIG. 2. In both FIGS. 1 and 2, bases which are inserted or changed relative to the other Figures are boxed, while deleted bases are indicated by an arrow. Both the DNA and amino acid sequences of FIG. 2 are believed to be correct.

According to the subject invention, novel recombinant DNA constructs are provided for the expression of a polypeptide having immunological activity corresponding to that of a naturally-occurring major outer membrane protein of *Chlamydia trachomatis*. Such polypeptides may find use as reagents in the detection of *Chlamydia trachomatis* or antibodies to *Chlamydia trachomatis*, and as vaccines against infection by *Chlamydia trachomatis* in susceptible hosts.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising a first DNA sequence segment encoding a polypeptide of at least 12 amino acids of the *Chlamydia trachomatis* major outer membrane protein (MOMP), operably linked to additional DNA sequence segments required for the expression of said first DNA sequence segment.

2. The DNA construct of claim 1, wherein the MOMP polypeptide encoded by the first DNA segment is from *C. trachomatis* serovar L2.

3. An isolated polynucleotide encoding a polypeptide of at least 12 amino acids of the *Chlamydia trachomatis* major outer membrane protein (MOMP).

4. The isolated polynucleotide of claim 3, wherein the MOMP polypeptide encoded thereby is from *C. trachomatis* serovar L2.

5. The isolated polynucleotide molecule of claim 3 encoding a *C. trachomatis* MOMP polypeptide, the sequence of said polynucleotide molecule comprising a coding strand for a MOMP polypeptide having an amino acid sequence as shown in FIG. 1 or FIG. 2.

6. The isolated polynucleotide molecule of claim 3 encoding a *C. trachomatis* MOMP polypeptide, the sequence of said polynucleotide molecule comprising a coding strand for a serovar variant of the MOMP polypeptide having an amino acid sequence as shown in FIG. 1 or FIG. 2.

7. A cultured cell line which expresses the *C. trachomatis* MOMP polypeptide encoded by the DNA construct of claim 1.

8. The cultured cell line of claim 7, which is eukaryotic.

9. The cultured cell line of claim 8, which is mammalian.

10. A method for producing a *C. trachomatis* MOMP polypeptide, comprising the steps of culturing the cell line of claim 7 and expressing the *C. trachomatis* MOMP polypeptide.

11. The method of claim 10, further comprising the step of purifying the *C. trachomatis* MOMP polypeptide which is expressed.

12. The DNA construct of claim 2, wherein the MOMP polypeptide encoded by the first DNA segment is from *C. trachomatis* serovar L2 as shown in FIG. 1 or FIG. 2.

13. The isolated polynucleotide of claim 2, wherein the MOMP polypeptide encoded thereby is from *C. trachomatis* serovar L2 as shown in FIG. 1 or FIG. 2.

\* \* \* \* \*